United States Patent
Nishijima et al.

(10) Patent No.: US 9,354,154 B2
(45) Date of Patent: May 31, 2016

(54) PARTICULATE MATTER AMOUNT DETECTION SYSTEM

(75) Inventors: Hiroki Nishijima, Suntou-gun (JP); Shinji Ikeda, Mishima (JP); Keiichiro Aoki, Suntou-gun (JP); Yoshinobu Yoshihara, Kusatsu (JP); Yasufumi Nakanishi, Kusatsu (JP); Takaya Suzuki, Kusatsu (JP)

(73) Assignees: TOYOTA JIDOSHA KABUSHIKI KAISHA, Toyota (JP); THE RITSUMEIKAN TRUST, Kyoto (JP)

( * ) Notice: Subject to any disclaimer, the term of this patent is extended or adjusted under 35 U.S.C. 154(b) by 652 days.

(21) Appl. No.: 13/503,585

(22) PCT Filed: Jun. 7, 2011

(86) PCT No.: PCT/IB2011/001244
§ 371 (c)(1),
(2), (4) Date: Apr. 23, 2012

(87) PCT Pub. No.: WO2011/154802
PCT Pub. Date: Dec. 15, 2011

(65) Prior Publication Data
US 2012/0211371 A1      Aug. 23, 2012

(30) Foreign Application Priority Data
Jun. 10, 2010   (JP) ................. 2010-133048

(51) Int. Cl.
*F02D 41/14*   (2006.01)
*G01N 15/06*   (2006.01)
*F01N 9/00*    (2006.01)

(52) U.S. Cl.
CPC ........... *G01N 15/0656* (2013.01); *F01N 9/002* (2013.01); *F01N 2410/00* (2013.01); *F01N 2560/05* (2013.01); *F01N 2560/20* (2013.01); *F02D 41/1466* (2013.01)

(58) Field of Classification Search
CPC . G01N 15/0656; F01N 9/002; F01N 2410/00; F01N 2560/05–2560/06; F02D 41/1466
USPC ................ 73/23.31, 23.33, 31.05, 31.06; 204/424–428
See application file for complete search history.

(56) References Cited

U.S. PATENT DOCUMENTS 4,687,715 A  *  8/1987  Michael .................. 429/498
2005/0180888 A1    8/2005  Pidria et al.
(Continued)

FOREIGN PATENT DOCUMENTS

DE          103 22 427 A1      12/2004
DE     10 2007 021 912 A1      11/2008
(Continued)

OTHER PUBLICATIONS

International Search Report issued in International Application No. PCT/IB2011/001244 dated Sep. 29, 2011.
(Continued)

*Primary Examiner* — Luan Van
*Assistant Examiner* — Maris R Kessel
(74) *Attorney, Agent, or Firm* — Oliff PLC

(57) ABSTRACT

A porous structure including a pair of electrodes disposed in a flow direction of exhaust gas and a solid electrolyte interposed between the electrodes is arranged in an exhaust passage of an internal combustion engine, and the amount of a particulate matter in exhaust gas is specified based on a potential difference generated between the electrodes.

11 Claims, 8 Drawing Sheets

(56) References Cited

U.S. PATENT DOCUMENTS

| | | | |
|---|---|---|---|
| 2008/0048681 A1* | 2/2008 | Birkhofer | F01N 9/002 |
| | | | 324/693 |
| 2010/0051458 A1* | 3/2010 | Teranishi et al. | 204/424 |
| 2010/0107737 A1 | 5/2010 | Krafthefer et al. | |

FOREIGN PATENT DOCUMENTS

| | | |
|---|---|---|
| DE | 10 2008 001 877 A1 | 11/2009 |
| EP | 1 566 623 A1 | 8/2005 |
| JP | 01163651 A * | 6/1989 |
| JP | A-11-218516 | 8/1999 |
| JP | A-2005-256717 | 9/2005 |
| JP | 2006266961 A * | 10/2006 |
| JP | A-2008-119618 | 5/2008 |
| JP | A-2008-261322 | 10/2008 |
| JP | A-2009-19557 | 1/2009 |
| WO | WO 2010/125636 A1 | 11/2010 |

OTHER PUBLICATIONS

Written Opinion issued in International Application No. PCT/IB2011/001244 dated Sep. 29, 2011.
Yoshihara et al., "Development of an On-Board PM Sensor for the OBD System Based on an Electrochemical Polorization", JSAE 20119319, SAE 2011-01-2059, 2011, 6 pages.

* cited by examiner

PARTICULATE MATTER AMOUNT DETECTION SYSTEM

BACKGROUND OF THE INVENTION

1. Field of the Invention

The invention relates to an art adopted in an exhaust passage of an internal combustion engine mounted on a vehicle to detect an amount of a particulate matter (PM) present in exhaust gas.

2. Description of Related Art

Conventionally, the amount of a particulate matter (PM) present in exhaust gas is be detected using a method that employs a sensor that includes an oxidation catalyst, a heater that heats the oxidation catalyst, and a temperature sensor that detects the temperature of the oxidation catalyst (e.g., see Japanese Patent Application Publication No. 2008-261322 (JP-A-2008-261322).

The references cited above use the amount of heat generated during the oxidization of the particulate matter collected by or deposited on the oxidation catalyst as a parameter. The related art aims at specifying the amount of the particulate matter collected by or deposited on the oxidation catalyst.

However, recent progress in exhaust gas purification has led to reductions in the diameter of particulate matter discharged from the internal combustion engine. Particularly when the detection device is arranged in the exhaust passage downstream of a particulate filter, the diameter of particulate matter leaking from the particulate matter is reduced.

Consequently, the oxidation catalyst may trap less than all the particulate matter in exhaust gas. In this case, the amount of particulate matter present in exhaust gas and the amount of the particulate matter collected by the oxidation catalyst are not closely correlated with each other. Thus, the accuracy in detecting the amount of the particulate matter decreases.

SUMMARY OF THE INVENTION

The invention provides an art capable of more accurately detecting the amount of a particulate matter present in exhaust gas of an internal combustion engine.

In the invention, a porous structure including a pair of electrodes disposed in a flow direction of exhaust gas and a solid electrolyte interposed between the electrodes is arranged in an exhaust passage of an internal combustion engine, and an amount of a particulate matter in exhaust gas is specified based on a potential difference generated between the electrodes.

A particulate matter amount detection system according to an aspect of the invention includes a first porous electrode provided in an exhaust passage of an internal combustion engine, a second porous electrode provided hi the exhaust passage downstream of the first electrode, a porous solid electrolyte interposed between the first electrode and the second electrode, a measurement portion that measures a potential difference between the first electrode and the second electrode, and a specification portion that specifies an amount of a particulate matter in exhaust gas based on the measured potential difference.

The particulate matter present in exhaust gas is collected by pores of the structure. In this case, the particulate matter present in exhaust gas is collected by an upstream region of the structure with respect to an exhaust gas flow direction (the first electrode and the solid electrolyte). Thus, at least part of the first electrode is covered with the particulate matter. As a result, a difference in oxygen partial pressure is generated between the first electrode and the second electrode. The aforementioned difference in oxygen partial pressure increases as the amount of the particulate matter with which the first electrode is covered increases (as the area of that region of the first electrode which is not covered with the particulate matter decreases).

In this case, when a difference in oxygen partial pressure is generated between the first electrode and the second electrode, polarization corresponding to the difference in oxygen partial pressure occurs. Therefore, a potential difference is generated between the first electrode and the second electrode. Consequently, the amount of the particulate matter collected by the structure can be calculated by measuring the potential difference between the electrodes.

It should be noted that since the structure according to the aspect of the invention is formed of the porous solid electrolyte and the porous electrodes, the small-diameter particulate matter in exhaust gas is also collected by the structure. As a result, the amount of the particulate matter present in exhaust gas and the amount of the particulate matter collected by the structure are closely correlated with each other. Consequently, as the amount of the particulate matter present in exhaust gas increases, the amount of the particulate matter collected by the structure increases. In other words, the amount of the particulate matter present in exhaust gas increases, the difference in oxygen partial pressure (the potential difference) between the electrodes increases.

In this case, the amount of the particulate matter in exhaust gas is specified from the potential difference between the electrodes by obtaining a relationship between the potential difference between the electrodes and the amount of the particulate matter in exhaust gas (e.g., a functional expression for converting the potential difference into the amount of the particulate matter, a map showing a relationship between the absolute magnitude of the potential difference and the absolute magnitude of the amount of the particulate matter, or the like) in advance through an adaptation operation utilizing an experiment or the like.

Accordingly, the particulate matter amount detection system according to the aspect of the invention makes it possible to more accurately specify the amount of the particulate matter present in exhaust gas. It should be noted that the function of the solid electrolyte as an electrolyte is activated when the temperature of the solid electrolyte is equal to or higher than an activation temperature. Thus, the temperature of the solid electrolyte may become lower than the activation temperature immediately after the cold start of the internal combustion engine or after the continuation of an operation state in which the temperature of exhaust gas is low (e.g., a deceleration operation state, an idle operation state, or the like). Thus, the particulate matter amount detection system according to the aspect of the invention may be equipped with a temperature adjustment portion that holds the temperature of the solid electrolyte equal to or higher than the activation temperature.

Meanwhile, when the amount of the particulate matter collected by the structure increases, the area of an exposed region of the first electrode (which is not covered with the particulate matter or can come into contact with exhaust gas) decreases, and the oxygen partial pressure in the first electrode and thereabound falls correspondingly. However, when the amount of the collected particulate matter exceeds a certain amount, the oxygen partial pressure does not fall any more. As a result, after the amount of the particulate matter collected by the structure exceeds a certain amount (e.g., the amount of the collected particulate matter at the time when the entire region of the first electrode is covered with the particulate matter), the potential difference between the electrodes and the amount of the particulate matter collected by the structure are not correlated with each other. Consequently, the amount of the particulate matter collected by the structure needs to be held smaller than a certain amount.

In this view, the particulate matter amount detection system according to the aspect of the invention may be equipped with a temperature adjustment portion that raises the temperature of the first electrode when the amount of the particulate matter collected by the structure reaches an upper-limit amount. The upper-limit amount mentioned herein is an amount obtained by subtracting a predetermined margin from the aforementioned certain amount. It should be noted that the aforementioned certain amount differs depending on the shape and size of the structure, the specification of the internal combustion engines or the like, and hence is desired to be calculated in advance through an experiment.

When the temperature of the first electrode is raised as soon as the amount of the particulate matter collected by the structure reaches the upper-limit amount, the particulate matter collected by the first electrode and the solid electrolyte is oxidized and removed. As a result, the amount of the particulate matter collected by the structure ran be held equal to or smaller than the certain amount.

As a method of determining whether the amount of the particulate matter collected by the structure has reached the upper-limit amount, it is possible to utilize a method of determining whether the potential difference between the electrodes has reached an upper limit. The upper limit is a value equivalent to the potential difference at the time when the amount of the collected particulate matter has reached the upper-limit amount.

As another method of determining whether the amount of the particulate matter collected by the structure has reached the upper-limit amount, it is possible to use a method of estimating art amount of the particulate matter present in exhaust gas based on an operation state of the internal combustion engine (a fuel injection amount, an intake air amount, an EGR gas amount, or the like) and determining whether an estimated value of the amount of is equal to or exceeds the upper-limit amount.

It should be noted that a method of estimating an amount of the particulate matter flowing out from a particulate filter based on an operation state of the internal combustion engine and a state of the particulate matter (a differential pressure across the particulate filter or a temperature thereof) and determining whether an estimated value of the amount is equal to or larger than the upper-limit amount can be used in a configuration in which the structure is arranged in the exhaust gas passage downstream of the particulate filter as the aspect of the invention.

However, if the temperature of the structure (especially the temperature around the first electrode) becomes high, the amount of the particulate matter oxidized per unit time may become excessively large with respect to the amount of the particulate matter collected per unit time. In this case, part of the particulate matter is oxidized without being collected by the structure. Therefore, the amount of the particulate matter in exhaust gas and the potential difference between the electrodes may not be closely correlated with each other any more. Consequently, the temperature of the structure needs to be adjusted such that the amount of the oxidized particulate matter does not exceed the amount of the collected particulate matter.

In this view, the temperature adjustment portion according to the aspect of the invention may lower the temperature of the first electrode when the amount of the particulate matter oxidized per unit time becomes larger than the amount of the particulate matter collected per unit time (or when the amount of the particulate matter oxidized per unit time is expected to become larger than the amount of the particulate matter collected per unit time). In this case, the amount of the particulate matter oxidized per unit time is small. Therefore, it is possible to avoid a circumstance in which the amount of the oxidized particulate matter becomes larger than the amount of the collected particulate matter.

As a method of determining whether the amount of the oxidized particulate matter is larger than the amount of the collected particulate matter, it is possible to utilize a method of determining whether the potential difference between the electrodes has decreased to a lower limit. The lower limit is a value obtained by adding a predetermined margin to the potential difference at the time when the amount of the oxidized particulate matter is larger than the amount of the collected particulate matter. Further, the lower limit may be a value obtained by adding a predetermined margin to the amount of the discharged particulate matter in an operation state in which the amount of the discharged particulate matter is the smallest among all the operation states of the internal combustion engine, or a value obtained by adding a predetermined margin to the amount of the particulate matter at the time when the amount of the particulate matter flowing out from the particulate filter is the smallest.

As another method of determining whether the amount of the oxidized particulate matter is larger than the amount of the collected particulate matter, it is possible to use a method of estimating the amount of the particulate matter present in exhaust gas based on the operation state of the internal combustion engine and the state of the particulate matter and determining whether a difference between an estimated value of the amount and the amount of the particulate matter specified by the specification portion (the specified value) (an amount obtained by subtracting the specified value from the estimated value) is larger than a permissible value. It should be noted that the permissible value is a value obtained by adding a predetermined margin to an error included in the aforementioned estimated value.

When the temperature of the structure is adjusted such that the potential difference between the electrodes is confined to a range between the upper limit and the lower limit as described above, the amount of the particulate matter in exhaust gas can be detected on a real-time basis and continuously.

It should be noted that the magnitude of the potential difference between the electrodes may change depending on the magnitude of the difference between the pressure to which the first electrode is exposed and the pressure to which the second electrode is exposed. Thus, it is also appropriate to specify a potential difference resulting from a pressure difference between the electrodes, and correct the measured value of the measurement portion with the specified potential difference. In this case, a relationship between the magnitude of the aforementioned pressure difference and the magnitude of the potential difference resulting from the pressure difference may be obtained in advance through an experiment.

When the measured value of the measurement portion is thus corrected with the pressure difference between the electrodes, the amount of the particulate matter in exhaust gas can be more accurately calculated.

Further, the magnitude of the potential difference between the electrodes may change depending on the magnitude of the difference between the air-fuel ratio of a gas to which the first electrode is exposed and the air-fuel ratio of a gas to which the second electrode is exposed. Thus, it is also appropriate to specify a potential difference resulting from the aforementioned difference between the air-fuel ratios, and correct the measured value of the measurement portion with the specified potential difference. In this case, a relationship between the aforementioned difference between the air-fuel ratios and the potential difference resulting from the difference between the air-fuel ratios may be obtained in advance through an experiment.

When the measured value of the measurement portion is thus corrected with the air-fuel ratio difference between the electrodes, the amount of the particulate matter in exhaust gas can be more accurately calculated.

It should be noted that only one of a correction processing based on the pressure difference between the electrodes and a correction processing based on the air-fuel ratio difference between the electrodes may be performed or both the correction processings may be performed. In the case where both the correction processings are performed, the accuracy in detecting the amount of the particulate matter can further be enhanced.

According to the aspect of the invention, the amount of the particulate matter present in exhaust gas of the internal combustion engine can be more accurately detected.

BRIEF DESCRIPTION OF THE DRAWINGS

The features, advantages, and technical and industrial significance of this invention will be described in the following detailed description of example embodiments of the invention with reference to the accompanying drawings, in which like numerals denote like elements, and wherein.

DETAILED DESCRIPTION OF EMBODIMENTS

Specific embodiments of the invention are described below with reference to the drawings. The dimensions, materials, shapes, relative arrangement, and the like of the components mentioned in these embodiments of the invention are not intended to limit the technical scope of the invention thereto unless otherwise stated.

Figure 1:
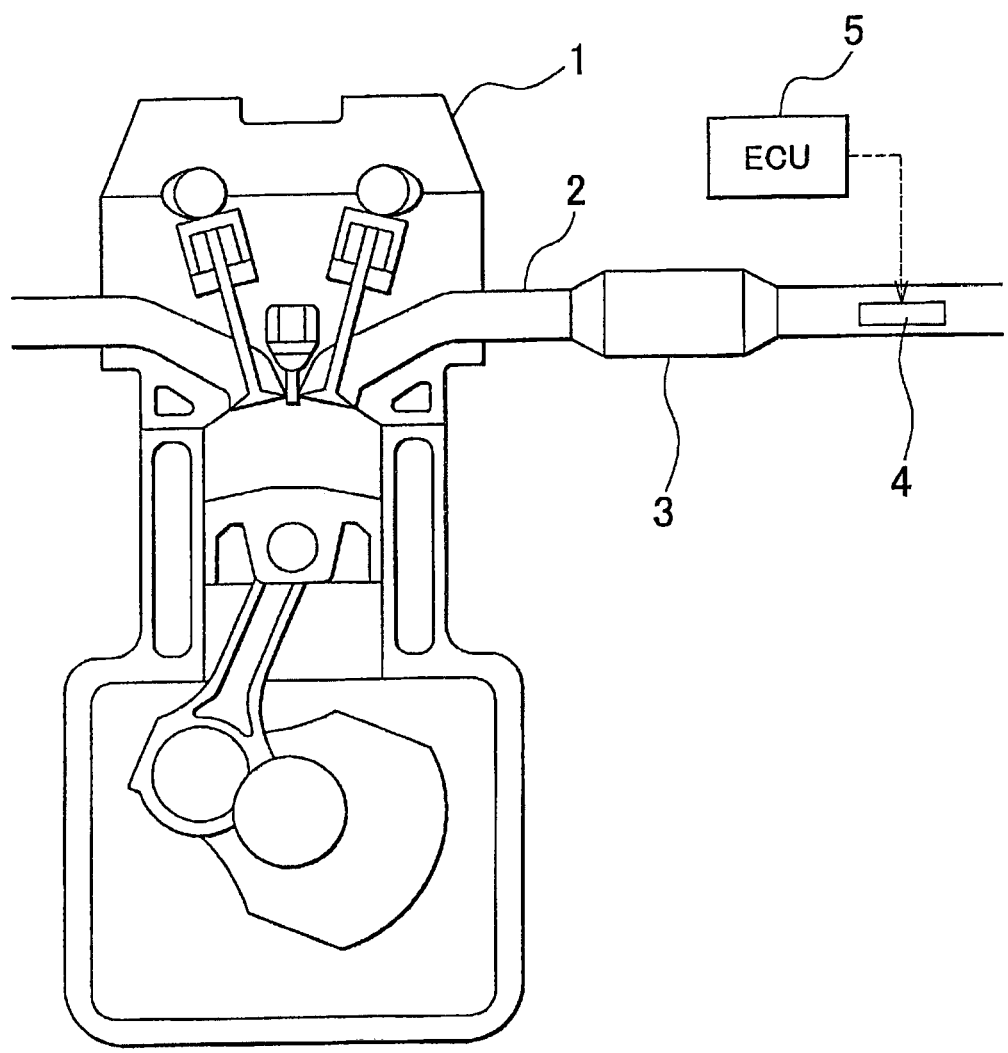
FIG. 1 shows the overall configuration of an internal combustion engine to which the invention is applied and an exhaust system thereof.

The first embodiment of the invention will be described with reference to FIGS. 1 to 4. FIG. 1 shows the overall configuration of an internal combustion engine to which the invention is applied and an exhaust system thereof.

The internal combustion engine 1 shown in FIG. 1 may be a compression ignition internal combustion engine (a diesel engine) or a spark ignition internal combustion engine (a gasoline engine). An exhaust pipe 2 is connected to the internal combustion engine 1. An exhaust gas purification device 3 containing an oxidation catalyst and a particulate filter is arranged at a midway position of the exhaust pipe 2. A measurement unit 4 that measures a physical quantity correlated with an amount of a particulate matter present in exhaust gas is provided in the exhaust pipe 2 downstream of the exhaust gas purification device 3.

Figure 2:
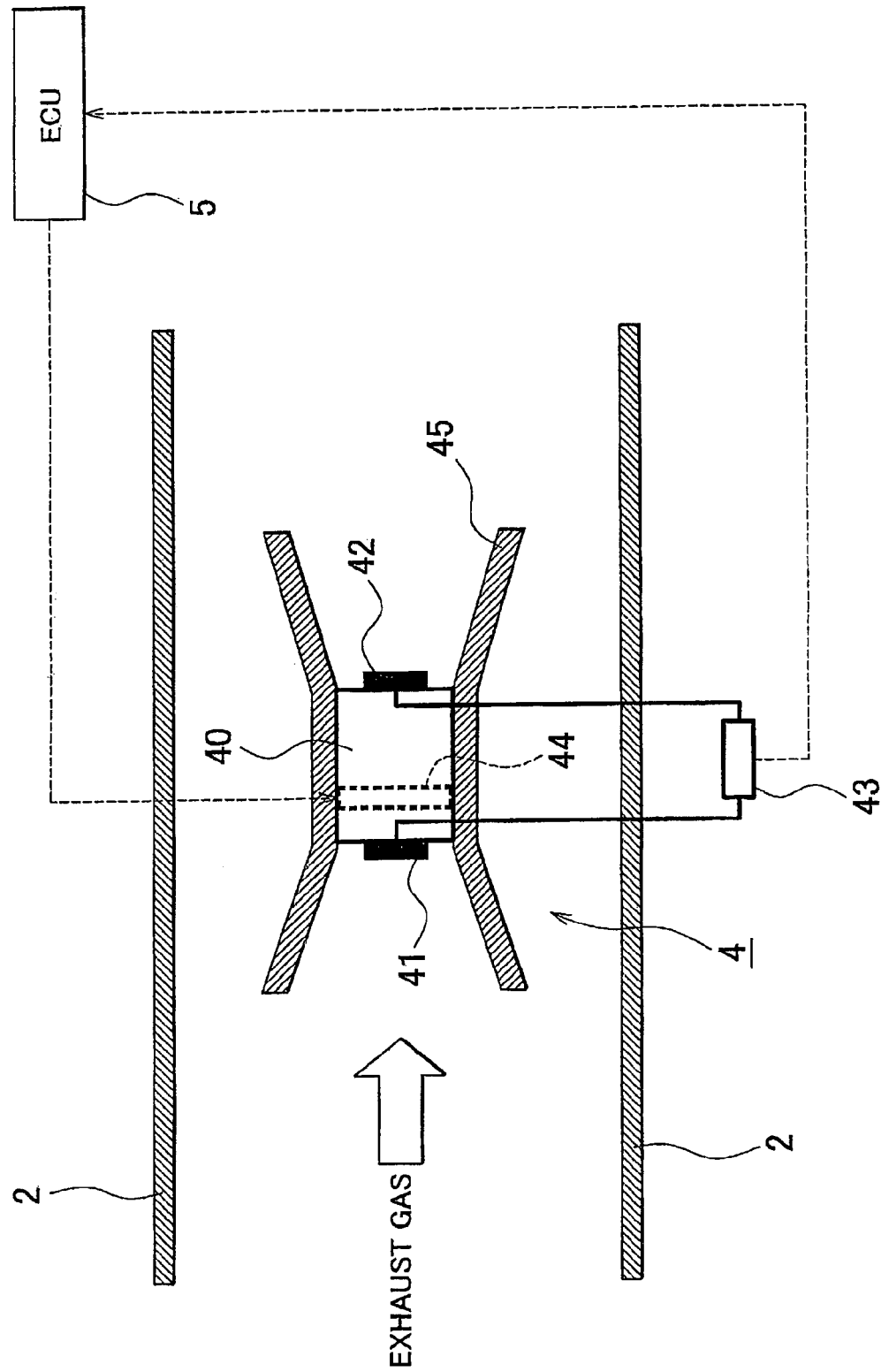
FIG. 2 is a longitudinal sectional view of the overall configuration of a measuring unit according to the first embodiment of the invention.
Figure 3:
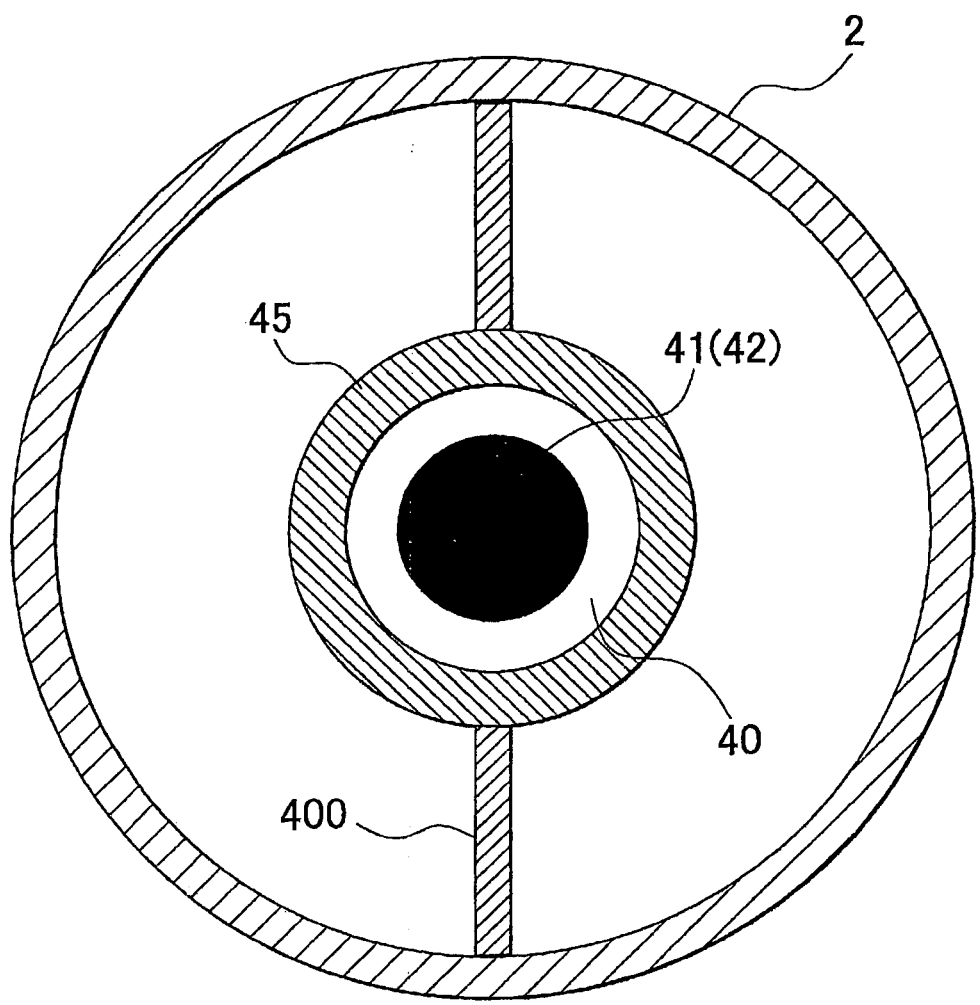
FIG. 3 is a transverse sectional view of the overall configuration of the measurement unit according to the first embodiment of the invention.

The configuration of the measurement unit 4 will now be described on the basis of FIGS. 2 and 3. FIG. 2 shows the cross-section (a longitudinal section) of the exhaust pipe 2 cut parallel to the axial direction thereof. FIG. 3 shows the cross-section (a transverse section) of the exhaust pipe 2 cut perpendicularly to its axial direction.

The measurement unit 4 is provided with a structure that includes a columnar solid electrolyte 40 and a pair of electrodes 41 and 42 provided at each end face of the solid electrolyte 40 respectively. The solid electrolyte 40 is a porous solid electrolyte having oxygen-ion conductivity, and may be formed of porous stabilized zirconia or the like. The electrodes 41 and 42 are porous electric conductors formed like membranes, and are formed of, for example, a porous metal.

A heater substrate 44, including a heat generator that generates heat when energized, is laminated on the solid electrolyte 40. The heater substrate 44 may be arranged and configured so that the entire region of the structure that includes the solid electrolyte 40 and the electrodes 41 and 42 can be heated, or may be arranged and configured so that one of the pair of the electrodes 41 and 42, that is, the electrode 41 and the solid electrolyte 40 can be heated by priority.

The above described structure may be fittingly inserted in a tubular duct 45, both ends of which are formed like a funnel. A strut 400 that protrudes from an inner wall face of the exhaust pipe 2 supports the duct 45 so that the duct 45 is coaxial with the exhaust pipe 2. In this case, as shown in FIG. 2, the duct 45 is arranged so that one of the electrodes 41 of the structure (hereinafter referred to as "the first electrode 41") is located on an upstream side in an exhaust gas flow direction (on the left side in FIG. 2) and the other electrode 42 (hereinafter referred to as "the second electrode 42") is located on a downstream side in the exhaust gas flow direction (on the right side in FIG. 2).

According to the arrangement shown in FIG. 2, the exhaust gas flowing into the duct 45 flows past the first electrode 41, the solid electrolyte 40, and the second electrode 42 in the stated sequence. Thus, particulate matter present in exhaust gas is collected by the first electrode 41 and the solid electrolyte 40. When the particulate matter is collected by the first electrode 41, at least part of the first electrode 41 is covered with the particulate matter. As a result, the partial pressure of oxygen around the first electrode 41 becomes lower than the partial pressure of oxygen around the second electrode 42. That is, a difference in the partial pressure of oxygen is generated between the first electrode 41 and the second electrode 42.

When a difference in oxygen partial pressure is generated between the first electrode 41 and the second electrode 42, polarization corresponding to the difference in oxygen partial pressure occurs. Therefore, a potential difference is generated between the first electrode 41 and the second electrode 42. In this case, as the amount of the particulate matter collected by or deposited on the first electrode 41 increases, the potential difference increases. The first electrode 41 and the solid electrolyte 40 are formed of porous materials. Therefore, the particulate matter present in exhaust gas can be substantially entirely collected. Consequently, the magnitude of the potential difference is closely correlated with the amount of the particulate matter present in exhaust gas.

Thus, the particulate matter amount detection system according to this embodiment of the invention includes a voltmeter 43 that is electrically connected to the first electrode 41 and the second electrode 42, and an ECU 5 that converts a reading of the voltmeter 43 into an amount of the particulate matter. The ECU 5 is an electronic control unit composed of a CPU, a ROM, a RAM, a backup RAM, and the like. It should be noted that the ECU 5 may also serve as an ECU for controlling the operational state of the internal combustion engine 1 or may be provided separately from the ECU for controlling the operation state of the internal combustion engine 1.

A relationship between the measured value of the voltmeter 43 and the amount of the particulate matter (e.g., an equation for calculating the amount of the particulate matter using the voltmeter reading, a map prescribing a relationship between an absolute magnitude of the voltmeter reading and an absolute magnitude of the amount of the particulate matter, or the like) is stored in the ROM of the ECU 5. The relationship between the reading of the voltmeter 43 and the amount of the particulate matter is determined in advance through an experiment or the like. Using the above equation or the map, the ECU 5 converts the reading of the voltmeter 43 into the amount of the particulate matter. The specification portion according to this embodiment of the invention is realized through this conversion of the reading of the voltmeter 43 into the amount of the particulate matter by the ECU 5. As a result, it is possible to accurately calculate the amount of the particulate matter in exhaust gas.

Meanwhile, the solid electrolyte 40 has a proper activation temperature. That is, the function of the solid electrolyte 40 as an electrolyte (oxygen-ion conductivity) is activated when the temperature of the solid electrolyte 40 is equal to or exceeds the activation temperature. Consequently, the temperature of the solid electrolyte 40 needs to be held equal to or above the activation temperature.

Thus, the ECU 5 energizes the heater substrate 44 (or increases the amount of energization of the heater substrate 44) when the temperature of the solid electrolyte 40 falls to a lower limit (a temperature obtained by adding a margin to the activation temperature). When the heater substrate 44 is thus controlled, the temperature of the solid electrolyte 40 is maintained at or above the activation temperature.

As a method of determining whether the temperature of the solid electrolyte 40 has fallen to the lower limit, it is possible to use a method of determining whether a measured value of a temperature sensor, which is installed to measure the temperature of the solid electrolyte 40, is equal to or lower than the lower limit.

As another method of determining whether the temperature of the solid electrolyte 40 has fallen to the lower limit, it is possible to use a method of determining whether a measured value of a temperature sensor, which is installed to measure the temperature of exhaust gas flowing into the structure or the temperature of exhaust gas flowing out from the structure, is equal to or lower than the lower limit.

It should be noted that when the temperature of the solid electrolyte 40 falls below the activation temperature, the potential difference between the first electrode 41 and the second electrode 42 becomes approximately equal to zero. Thus, the ECU 5 determines that if the temperature of the solid electrolyte 40 is below the activation temperature when the reading of the voltmeter 43 is zero or close to zero. According to this method, it is not necessary to provide a temperature sensor. Therefore, an improvement in vehicle mountability and a reduction in manufacturing cost is also achieved.

Further, when the amount of the particulate matter collected by or deposited on the first electrode 41 and the solid electrolyte 40 (hereinafter referred to as the "the collected amount of particulate matter") exceeds a certain amount, the first electrode 41 is entirely covered with the particulate matter. As a result, once the amount of the collected particulate matter exceeds the certain amount, the potential of the first electrode 41 hardly changes even when the amount of the collected particulate matter further increases. That is, after the amount of the collected particulate matter exceeds the certain amount, the reading of the voltmeter 43 is no longer closely correlated with the amount of the collected particulate matter. Furthermore, when the amount of the collected particulate matter exceeds the certain amount, clogging of the structure may occur, which causes an increase in pressure loss (back pressure). Accordingly, it is necessary to maintain the amount of the collected particulate matter below the certain amount.

Thus, when the amount of the collected particulate matter reaches an upper-limit amount, the ECU 5 energizes the heater substrate 44 (or increases the amount of energization of the heater substrate 44) to oxidize and remove the particulate matter collected by or deposited on the first electrode 41 and the solid electrolyte 40. The "upper-limit amount" mentioned herein is the amount obtained by subtracting a predetermined margin from the certain amount. When the heater substrate 44 is thus controlled, the amount of the collected particulate matter is maintained below the certain amount.

A method of determining whether the reading of the voltmeter 43 has reached a maximum threshold value may be used to determine whether the amount of collected particulate matter has reached the upper-limit amount. In the context of the voltmeter, the upper-limit amount is the potential difference between the first electrode 41 and the second electrode 42 when the amount of collected particulate matter has reached the upper-limit amount.

Alternatively, whether the amount of the collected particulate matter has reached the upper-limit amount may be determined by estimating the amount of the particulate matter flowing into the structure based on the operating state of the internal combustion engine 1 (a fuel injection amount, an intake air amount, an EGR gas amount, or the like) and the condition of a particulate filter (a differential pressure across the particulate filter or a temperature thereof), and then determining whether the estimated value is equal to or exceeds the upper-limit amount.

It should be noted that after the amount of the collected particulate matter reaches the threshold amount, the reading of the voltmeter 43 does not change. Thus, the ECU 5 may also determine that the amount of the collected particulate matter has reached the threshold amount when the amount of change in the reading of the voltmeter 43 is equal to or below a threshold amount of change.

However, when the temperature of the structure (especially the temperature of the first electrode 41 and the solid electrolyte 40) becomes high, the amount of the particulate matter oxidized per unit time may become large with respect to the amount of the particulate matter collected per unit time. In other words, the amount of the particulate matter oxidized per unit time may become large with respect to the amount of the particulate matter flowing into the structure per unit time. In this case, a portion of the particulate matter is oxidized without being collected by the structure. Therefore, the measured value of the voltmeter 43 and the amount of the particulate matter in exhaust gas may not be closely correlated with each other. Consequently, it is necessary to maintain the particulate matter oxidation rate below the particulate matter collection rate.

Thus, when the amount of the particulate matter oxidized per unit time becomes larger than the amount of the particulate matter collected per unit time, the ECU 5 stops the heater substrate 44 (or reduces the amount of energization of the heater substrate 44) to lower the temperature of the structure. When the heater substrate 44 is thus controlled, it is possible to avoid a circumstance in which the amount of the particulate matter oxidized per unit time becomes larger than the amount of the particulate matter collected per unit time.

As a method of determining whether the amount of the particulate matter oxidized per unit time is larger than the amount of the particulate matter collected per unit time, it is possible to utilize a method of determining whether the measured value of the voltmeter 43 has decreased to a lower limit. The "lower limit" is obtained by adding a predetermined margin to the potential difference between the first electrode 41 and the second electrode 42 when the amount of the oxidized particulate matter exceeds the amount of the collected particulate matter.

Another method of determining whether the amount of the particulate matter oxidized per unit time is larger than the amount of the particulate matter collected per unit is to estimate the amount of the particulate matter flowing into the structure based on the operating state of the internal combustion engine 1 and the state of the particulate matter and compare the estimated amount of particulate matter with the amount of the particulate matter specified from the measured value of the voltmeter 43 (the specified value).

If the particulate matter oxidation rate exceeds the particulate matter collection rate, the specified value becomes smaller than the amount of the particulate matter flowing into the structure. Thus, it is possible to determine that the rate at which particulate matter oxidized per unit time exceeds the rate at which particulate matter is collected when the difference between the estimated amount of the particulate matter flowing into the structure and the specified value exceeds a permissible value (a value obtained by subtracting the specified value from the estimated value).

The ECU 5 controls the heater substrate 44 as described above, and the temperature adjustment portion according to the invention is thereby realized. As a result, the amount of the particulate matter present in exhaust gas can be detected in real-time. Accordingly, the particulate matter amount detection system according to this embodiment of the invention makes can accurately detect the amount of the particulate matter present in exhaust gas in real-time.

Although the structure that includes the electrodes 41 and 42 and the solid electrolyte 40 is provided in the duct 45 in the configuration of the above embodiment, the structure may be positioned directly in the exhaust pipe 2 instead. However, if the structure is provided directly in the exhaust pipe 2, the detection accuracy may decrease due to the fluctuations in the flow rate of exhaust gas (the flow velocity of exhaust gas), the pulsation of exhaust gas, and the like.

Figure 4:
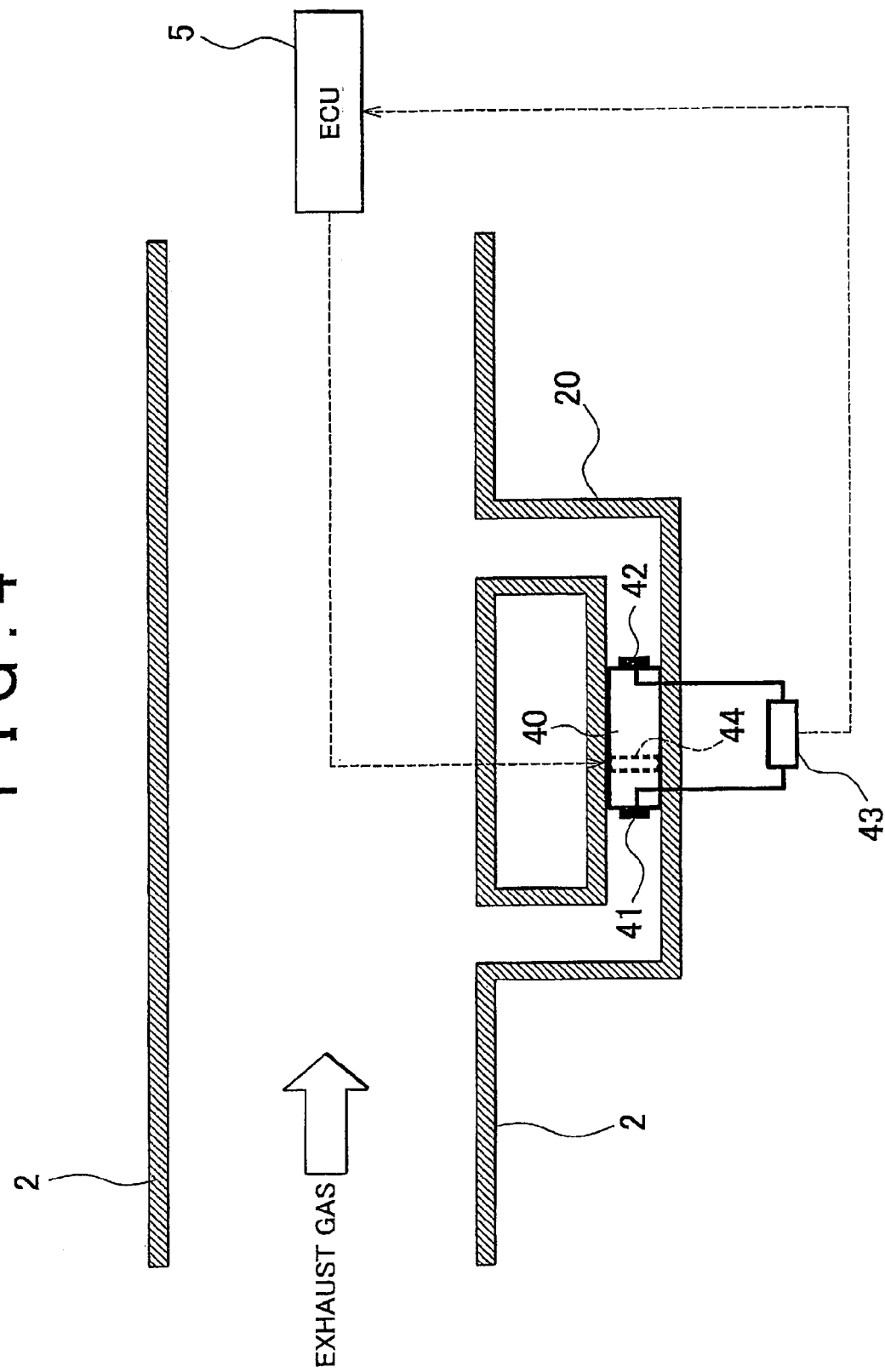
FIG. 4 shows an alternative arrangement of the measurement unit.

Consequently, as shown in FIG. 4, it is also appropriate to fit the exhaust pipe 2 with a bypass pipe 20 bypassing part of the exhaust pipe 2, and arrange the structure in the bypass pipe 20. When the structure is thus arranged in the bypass pipe 20, the amount of the particulate matter may be detected without increasing backpressure in the exhaust pipe 2. In this case, it is appropriate to provide a pump that draws exhaust gas in the exhaust pipe 2 into the bypass pipe 20 to stabilize the flow rate of exhaust gas in the bypass pipe 20.

Next, the second embodiment of the invention will be described on the basis of FIGS. 5 and 6. The differences in configuration from that of the first embodiment of the invention will now be described, parts of the configuration that otherwise remain substantially the same will not be described.

This embodiment of the invention differs from the first embodiment of the invention in that the reading of the voltmeter 43 is corrected in accordance with the difference between the pressure around the first electrode 41 and the pressure around the second electrode 42.

The potential difference between the first electrode 41 and the second electrode 42 changes in accordance with the magnitude of the difference between the pressure to which the first electrode 41 is exposed and the pressure to which the second electrode 42 is exposed. For example, when the pressure around the first electrode 41 is higher than the pressure around the second electrode 42, the potential difference between the first electrode 41 and the second electrode 42 decreases. Thus, when the pressure around the first electrode 41 is higher than the pressure around the second electrode 42, the potential difference measured by the voltmeter 43 is lower than the expected potential difference for a given difference in oxygen partial pressure.

Thus, the particulate matter amount detection system according to this embodiment of the invention specifies an offset amount of the potential difference resulting from the aforementioned pressure difference (hereinafter referred to as the "potential difference offset amount"), and corrects the potential difference measured by the voltmeter 43 with the specified potential difference offset amount.

Figure 5:
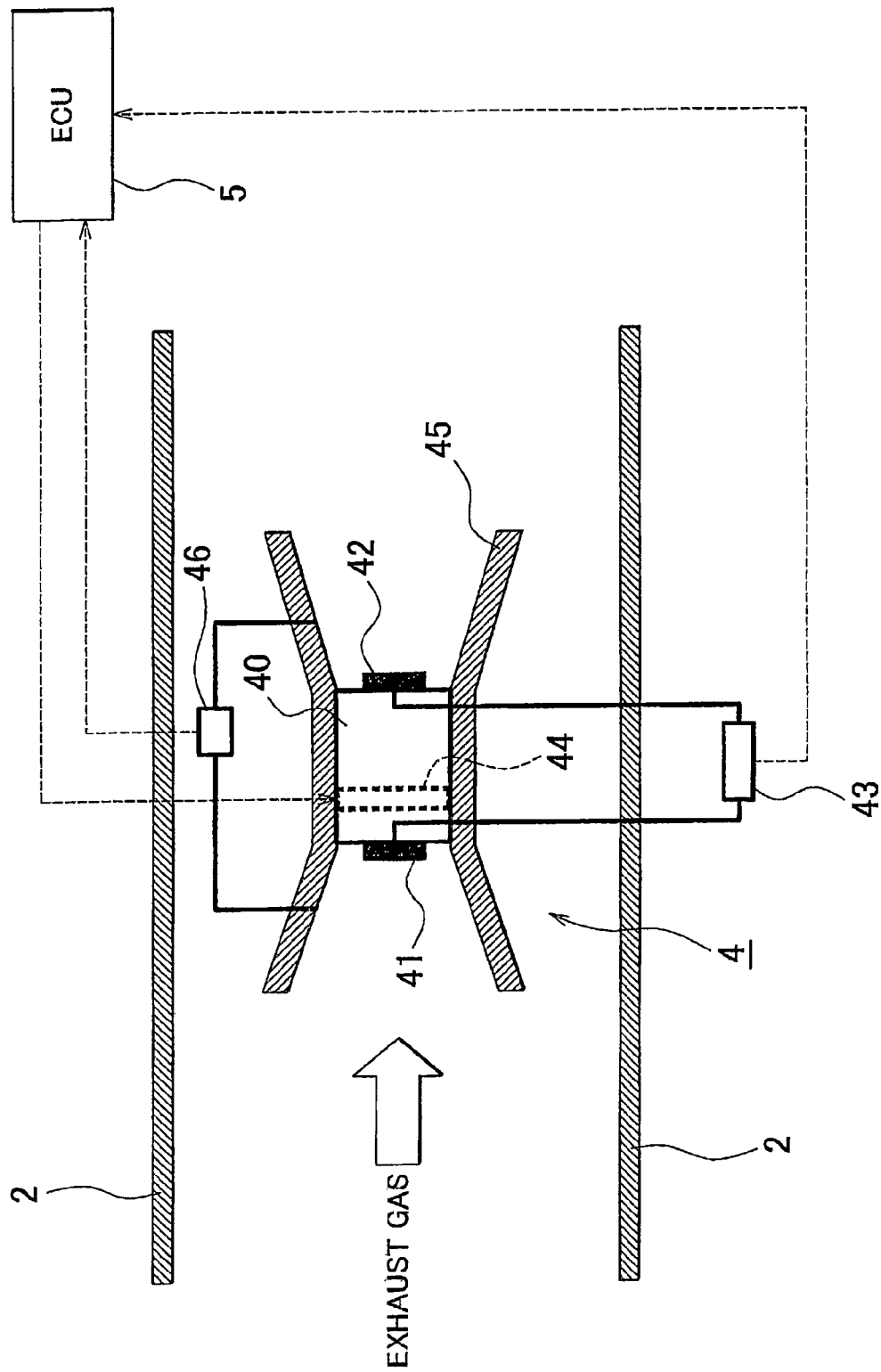
FIG. 5 is a longitudinal sectional view of the configuration of a measurement unit according to the second embodiment of the invention.

FIG. 5 is a longitudinal sectional view showing the configuration of the measurement unit according to this embodiment of the invention. As shown in FIG. 5, the duct 45 of the measurement unit 4 is fitted with a differential pressure sensor 46 that measures the differential pressure (which is obtained by subtracting the pressure at the downstream side from the pressure at the upstream side) $\Delta P$ between the pressure in the duct 45 at a position upstream of the solid electrolyte 40 and the pressure in the duct 45 at a position downstream of the solid electrolyte 40. The measured value (the differential pressure) $\Delta P$ of the differential pressure sensor 46 is input to the ECU 5. It should be noted that the duct 45 may be also fitted with two pressure sensors instead of the differential pressure sensor 46 to calculate a difference between measured values of those pressure sensors.

The ECU 5 determines a potential difference offset amount $\Delta v$ on the basis of the measured value (the differential pressure) $\Delta P$ of the differential pressure sensor 46, and adds the determined potential difference offset amount $\Delta v$ to the measured value V of the voltmeter 43 (V+$\Delta v$).

Figure 6:
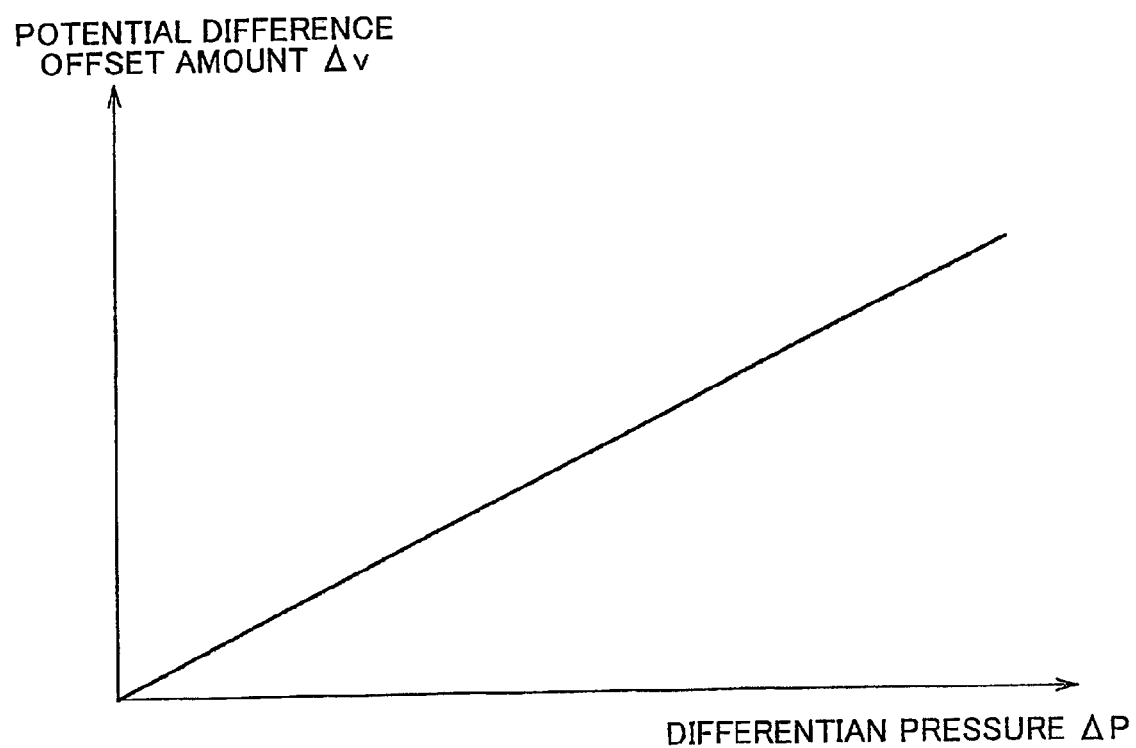
FIG. 6 is a graph of the relationship between a differential pressure and a potential difference offset amount.

In this case, the ECU 5 determines the potential difference offset amount $\Delta v$ using a map as shown in FIG. 6. FIG. 6 is a view schematically showing a map prescribing a relationship between the potential difference offset amount $\Delta v$ and the differential pressure $\Delta P$. In FIG. 6, the potential difference offset amount $\Delta v$ when the differential pressure $\Delta P$ is high than when the differential pressure $\Delta P$ is low. This is because the potential difference between the first electrode 41 and the second electrode 42 is smaller when the differential pressure $\Delta P$ is high than when the differential pressure $\Delta P$ is low, as described above.

When the measured value V of the voltmeter 43 is corrected according to this method, the potential difference corresponding to the difference in oxygen partial pressure can be accurately calculated even in the case where a difference in pressure is generated between the first electrode 41 and the second electrode 42.

Next, a third embodiment of the invention will be described on the basis of FIGS. 7 and 8. Only the configurational details different from those of the foregoing first embodiment of the invention will be described, and the configurational details similar thereto will not be described.

This embodiment of the invention is differs from the first embodiment of the invention in that the reading of the voltmeter 43 is corrected in accordance with the difference between the air-fuel ratio around the first electrode 41 and the air-fuel ratio around the second electrode 42.

The potential difference between the first electrode 41 and the second electrode 42 may change depending on the magnitude of the difference between the air-fuel ratio of an atmosphere to which the first electrode 41 is exposed and the air-fuel ratio of an atmosphere to which the second electrode 42 is exposed. For example, when the air-fuel ratio around the first electrode 41 is higher than the air-fuel ratio around the second electrode 42, the oxygen partial pressure around the first electrode 41 is high, and therefore, the potential difference between the first electrode 41 and the second electrode 42 is small. Thus, when the air-fuel ratio around the first electrode 41 is higher than the air-fuel ratio around the second electrode 42, the measured value of the voltmeter 43 is smaller than the expected potential difference for a given difference in oxygen partial pressure.

In contrast, when the air-fuel ratio around the first electrode 41 is lower than the air-fuel ratio around the second electrode 42, the oxygen partial pressure around the first electrode 41 is low, and therefore, the potential difference between the first electrode 41 and the second electrode 42 is large. Thus, when the air-fuel ratio around the first electrode 41 is lower than the air-fuel ratio around the second electrode 42, the measured value of the voltmeter 43 is larger than the expected potential difference for a given difference in oxygen partial pressure.

Thus, the particulate matter amount detection system according to this embodiment of the invention specifies a correction coefficient for the potential difference resulting from the air-fuel ratio difference, and corrects the measured value of the voltmeter 43 with the specified correction coefficient.

Figure 7:
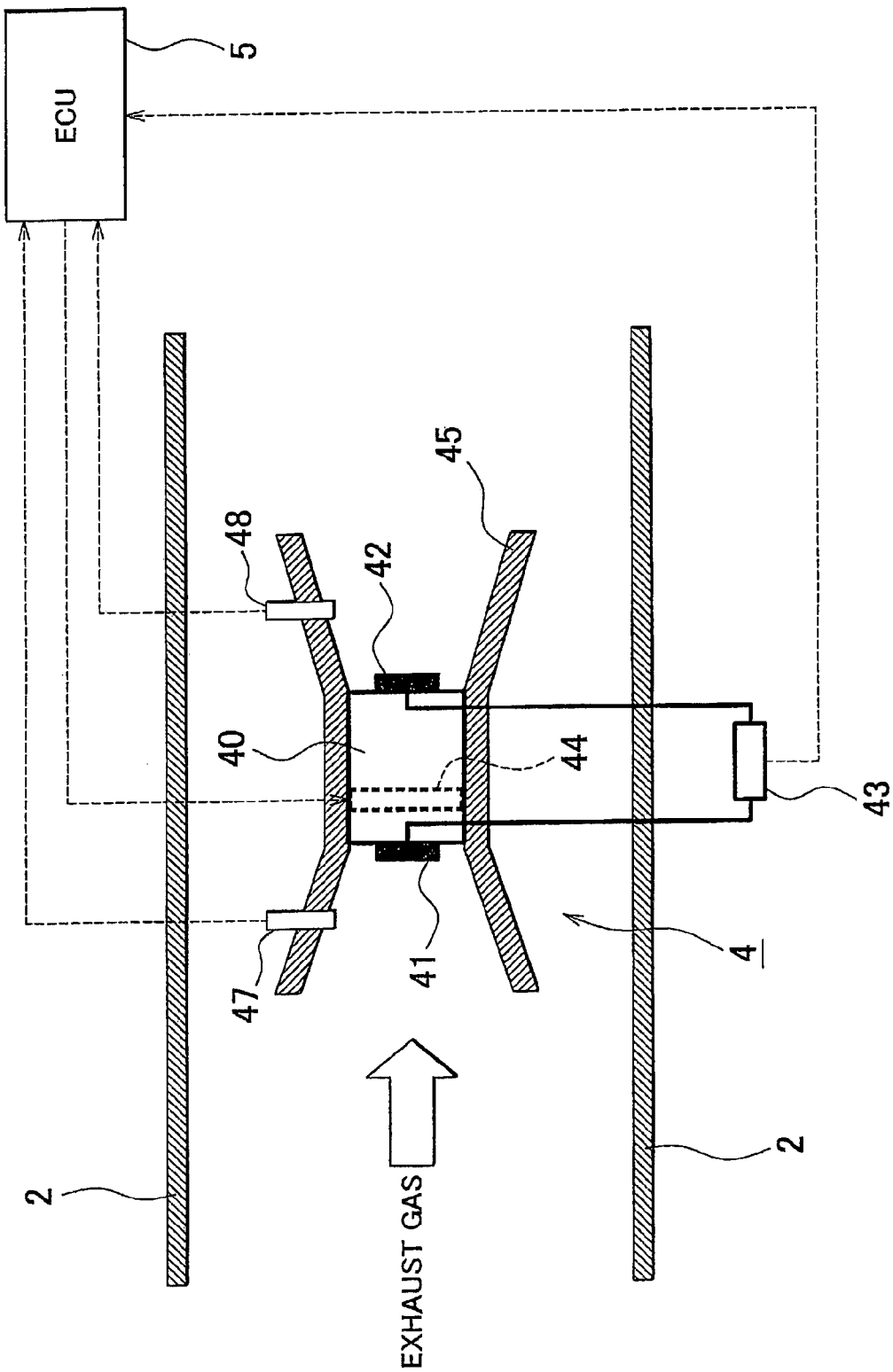
FIG. 7 is a longitudinal sectional view of the configuration of a measurement unit according to the third embodiment of the invention.

FIG. 7 is a longitudinal sectional view showing a configuration of the measurement unit 4 according to this embodiment of the invention. As shown in FIG. 7, the duct 45 of the measurement unit 4 is fitted with a first air-fuel ratio sensor 47 that measures the air-fuel ratio in the duct 45 at a position upstream of the solid electrolyte 40 5 and a second air-fuel ratio sensor 48 that measures the air-fuel ratio in the duct 45 at a position downstream of the solid electrolyte 40. The air-fuel ratios detected by the first air-fuel ratio sensor 47 and the second air-fuel ratio sensor 48 are input to the ECU 5.

The ECU 5 determines the correction coefficient α based on the ratio (af1/af2) of the upstream air-fuel ratio af1 measured by the first air-fuel ratio sensor 47 to the downstream air-fuel ratio af2 measured by the second air-fuel ratio sensor 48, and multiplies the measured value V of the voltmeter 43 by the determined correction coefficient α (V*α).

Figure 8:
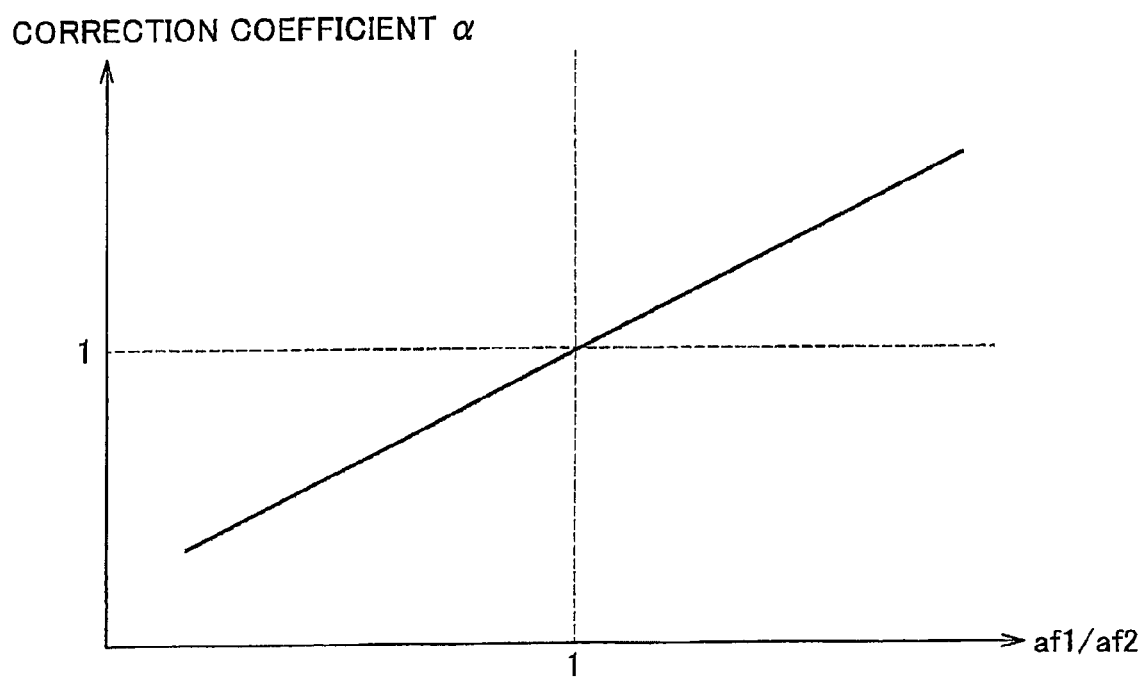
FIG. 8 is a graph that depicts the relationship between an air-fuel ratio quotient and a correction coefficient.

In this case, the ECU 5 determines the correction coefficient α using a map as shown in FIG. 8. FIG. 8 is a view schematically showing a map prescribing a relationship between the aforementioned ratio between the air-fuel ratios (af1/af2) and the correction coefficient α. In FIG. 8, the correction coefficient α is larger when the ratio (af1/af2) is large, than when the ratio (af1/af2) is small. Furthermore, when the ratio (af1/af2) is below "1", the correction coefficient α is also set to a value lower than "1". If the ratio (af1/af2) is above "1", the correction coefficient α is also set to a value greater than "1". This is because the potential difference between the first electrode 41 and the second electrode 42 is small when the ratio (af1/af2) is larger than "1", and the potential difference between the first electrode 41 and the second electrode 42 is large when the ratio (af1/af2) is smaller than "1".

If the measured value V of the voltmeter 43 is corrected according to this method, the potential difference corresponding to the difference in oxygen partial pressure can be accurately calculated even if a difference in air-fuel ratio is generated between the first electrode 41 and the second electrode 42. As a result, the amount of the particulate matter in exhaust gas can be accurately calculated.

It should be noted that the correction based on the pressure difference as described in the second embodiment of the invention and the correction based on the air-fuel ratio difference as described in the third embodiment of the invention may be carried out in combination with each other. In this case, the amount of the particulate matter in exhaust gas can be accurately calculated even when a difference in pressure or a difference in air-fuel ratio is generated between the first electrode 41 and the second electrode 42.

The invention claimed is:

1. A particulate matter amount detection system comprising:
   a first porous electrode provided in an exhaust passage of an internal combustion engine;
   a second porous electrode provided in the exhaust passage downstream of the first electrode;
   a porous solid electrolyte interposed between the first electrode and the second electrode;
   a measurement device configured to measure a potential difference between the first electrode and the second electrode;
   a specification unit programmed to specify an amount of a particulate matter in exhaust gas based on the measured potential difference such that an increased measured potential difference correlates to an increased amount of the particulate matter in the exhaust gas; and
   a temperature controller programmed to adjust a temperature of the first electrode,
   wherein the temperature controller raises the temperature of the first electrode when the measured potential difference reaches a predetermined upper limit to thereby oxide and remove the particulate matter collected by or deposited on the first electrode and the solid electrolyte, and lowers the temperature of the first electrode when the measured potential difference decreases to a predetermined lower limit.

2. The particulate matter amount detection system according to claim 1, further comprising
   an estimator programmed to estimate the amount of the particulate matter present in exhaust gas based on an operation state of the internal combustion engine,
   wherein the temperature controller lowers the temperature of the first electrode when the amount of the particulate matter specified by the specification unit is smaller than the estimated amount of the particulate matter and a difference between the estimated amount of the particulate matter and the specified amount of the particulate matter exceeds a certain value.

3. The particulate matter amount detection system according to claim 1, wherein the specification unit is programmed to correct the potential difference measured by the measurement device based on a pressure difference between the first electrode and the second electrode, and programmed to specify the amount of the particulate matter in exhaust gas based on the corrected potential difference.

4. The particulate matter amount detection system according to claim 1, wherein the porous solid electrolyte includes pores configured to allow exhaust gas to pass through the solid electrolyte from the first electrode to the second electrode.

5. A particulate matter amount detection system comprising:
- a first porous electrode provided in an exhaust passage of an internal combustion engine;
- a second porous electrode provided in the exhaust passage downstream of the first electrode;
- a porous solid electrolyte interposed between the first electrode and the second electrode;
- a measurement device configured to measure a potential difference between the first electrode and the second electrode; and
- a specification unit programmed to specify an amount of a particulate matter in exhaust gas based on the measured potential difference such that an increased measured potential difference correlates to an increased amount of the particulate matter in the exhaust gas,
- wherein the specification unit is programmed to correct the potential difference measured by the measurement device based on an air-fuel ratio difference between the first electrode and the second electrode, and programmed to specify the amount of the particulate matter in exhaust gas based on the corrected potential difference.

6. The particulate matter amount detection system according to claim 5, wherein the porous solid electrolyte includes pores configured to allow exhaust gas to pass through the solid electrolyte from the first electrode to the second electrode.

7. A method of controlling a particulate matter amount detection system that includes a first porous electrode provided in an exhaust passage of an internal combustion engine, a second porous electrode provided in the exhaust passage downstream of the first electrode, a porous solid electrolyte interposed between the first electrode and the second electrode, a temperature controller, a measurement device, and a specification unit, the method comprising:
- adjusting a temperature of the first electrode;
- measuring a potential difference between the first electrode and the second electrode; and
- specifying an amount of a particulate matter in exhaust gas based on the measured potential difference such that an increased measured potential difference correlates to an increased amount of the particulate matter in the exhaust gas,
- wherein the temperature controller raises the temperature of the first electrode when the measured potential difference reaches a predetermined upper limit to thereby oxide and remove the particulate matter collect by or deposited on the first electrode and the solid electrolyte, and lowers the temperature of the first electrode when the measured potential difference decreases to a predetermined lower limit.

8. The method of controlling a particulate matter amount detection system according to claim 7, wherein the particulate matter amount detection system further includes an estimator, and
the temperature controller lowers the temperature of the first electrode when the amount of the particulate matter specified by the specification unit is smaller than the estimated amount of the particulate matter and a difference between the estimated amount of the particulate matter and the specified amount of the particulate matter exceeds a certain value.

9. The method of controlling a particulate matter amount detection system according to claim 7, wherein the specification unit is programmed to correct the potential difference measured by the measurement device based on a pressure difference between the first electrode and the second electrode, and programmed to specify the amount of the particulate matter in exhaust gas based on the corrected potential difference.

10. The method of controlling a particulate matter amount detection system according to claim 7, wherein the specification unit is programmed to correct the potential difference measured by the measurement device based on an air-fuel ratio difference between the first electrode and the second electrode, and programmed to specify the amount of the particulate matter in exhaust gas based on the corrected potential difference.

11. The method of controlling a particulate matter amount detection system according to claim 7, wherein the porous solid electrolyte includes pores configured to allow exhaust gas to pass through the solid electrolyte from the first electrode to the second electrode.

* * * * *